United States Patent [19]

Segawa et al.

[11] 4,294,801
[45] Oct. 13, 1981

[54] GAS COMPONENT DETECTOR

[75] Inventors: Yoshihiro Segawa, Okazaki; Minoru Ohta, Anjo; Eturo Yasuda, Okazaki, all of Japan

[73] Assignee: Nippon Soken, Inc., Nishio, Japan

[21] Appl. No.: 169,162

[22] Filed: Jul. 15, 1980

Related U.S. Application Data

[63] Continuation of Ser. No. 20,927, Mar. 15, 1979, abandoned.

[30] Foreign Application Priority Data

Mar. 24, 1978 [JP] Japan ................................. 53/38196

[51] Int. Cl.³ ............................................. G01N 27/04
[52] U.S. Cl. ................................... 422/98; 23/238 E; 324/71 SN; 338/22 SD; 340/634; 422/90
[58] Field of Search ............................. 422/90, 94–98; 338/22 SD, 34; 324/71 SN; 60/276; 204/195 S

[56] References Cited

U.S. PATENT DOCUMENTS

| | | | |
|---|---|---|---|
| 3,459,765 | 5/1976 | Stewart | 338/34 |
| 4,001,758 | 1/1977 | Esper | 338/34 |
| 4,066,413 | 1/1978 | Segawa et al. | 422/98 |
| 4,099,922 | 7/1978 | Yasuda et al. | 422/95 |
| 4,147,513 | 4/1979 | Bienkowski et al. | 422/98 X |
| 4,151,503 | 4/1979 | Cermak | 338/22 SD X |

FOREIGN PATENT DOCUMENTS 2724152 8/1977 Fed. Rep. of Germany.

*Primary Examiner*—Michael S. Marcus
*Attorney, Agent, or Firm*—Cushman, Darby & Cushman

[57] ABSTRACT

A gas component detector for detecting a gas component in the exhaust gases includes a detector element of a metal oxide whose electrical resistance value varies suddenly depending on the gas component. The detector element is held on an electrically insulating and heat-resistant holding body and furthermore, the detector element is enclosed by a catalyst carrier body which is fixed to the holding body by an inorganic bonding adhesive. Since the catalyst carrier body is of a porous heat-resistant metal oxide, the exhaust gases to be detected are permitted to pass through the catalyst carrier body and the gas component is oxidated by the aid of a catalyst material carried on the carrier body. The environment of the detector element thus becomes a weak reducing environment thereby preventing the detector element from being reduced and deteriorated.

4 Claims, 13 Drawing Figures

GAS COMPONENT DETECTOR

This is a continuation of application Ser. No. 20,927 filed Mar. 15, 1979 (now abandoned).

BACKGROUND OF THE INVENTION

1. FIELD OF THE INVENTION

This invention relates to a gas component detector suitable for use in an exhaust gas purifying system of the feedback type employing a three-way catalyst.

2. DESCRIPTION OF THE PRIOR ART

Hitherto, as a gas component detector for internal combustion engines, there have been several detectors which employ a sintered body of a metal oxide in which an electrical resistance value changes depending upon a partial pressure of oxygen in the environment. Recently, as a countermeasure against the polluting components in the exhaust gases of the internal combustion engine of automobiles, etc., purifying systems using a three-way catalyst for removing simultaneously the harmful components, CO, HC, and $NO_x$, have been considered. Among these purifying systems one is a suction control system which controls the amount of suction air or fuel at the suction side, and another is an exhaust control system in which the air-fuel ratio (hereinafter referred to as A/F ratio) at the suction side is set richer than the ideal A/F ratio and secondary air is supplied to the exhaust gases, and the amount of the secondary air is controlled. In both cases, in order to enable the three-way catalyst to function effectively at a maximum degree, it is necessary to control the A/F ratio either at the suction side or at the exhaust side so as to keep the A/F ratio in a very narrow effective range, W, of the three-way catalyst as shown in FIG. 1, and for this purpose a sensor is necessary to sense the gas component of the exhaust gases and to detect the A/F ratio thereof. And by the use of the output signal of the sensor, the amount of air or fuel at the suction side is controlled, or the amount of secondary air supplied to the exhaust gases is controlled thereby to maintain the A/F ratio within the effective range of the three-way catalyst (W in FIG. 1), and thereby to eliminate the harmful components in the exhaust gases.

However, the gas component detector using a metal oxide among the above-mentioned gas component detectors, has the disadvantage that the metal oxide itself will be reduced (deoxidated) over a long duration in a reducing atmosphere at high temperatures, and also the electrical resistance in the oxidating atmosphere side will drop to a large extent resulting in a change of the inherent properties thereof. Furthermore, there is another disadvantage that when this gas component detector is used in the exhaust control system, a position at which the characteristics change rapidly will be shifted from the stoichiometric A/F ratio to the lean side largely as shown in FIG. 2 and hence it will be impossible to make the three-way catalyst function effectively.

The problem that the forementioned gas component detector is reduced in a high temperature and reducing atmosphere is supposed to be due to the existence of reducing gases ($H_2$, CO, HC) and carbon. In other words, although the reducing gas itself has a reducing property to some extent, if the carbon coexists therewith, the reducing property is doubled, and results in a phenomenon in which a detector element of metal oxide is reduced at high temperatures and an electrical resistance value at the oxidating atmosphere side drops. Furthermore, a main cause for the forementioned disadvantages in the exhaust control system is considered to be due to the effect of unburned components, specially, $H_2$ and CO in the exhaust gases. FIGS. 3a, 3b and 3c show the characteristics of the detector in the model gases of the $H_2$-air system, CO-air system and i-$C_4H_{10}$-air system respectively. As will be seen from these figures, both $H_2$ and CO change their characteristics suddenly in the oxidating atmosphere side, and especially the effect of $H_2$ is significant. Since the A/F ratio in the suction side is set to be rich in the exhaust control system, as will be seen from FIG. 4, $H_2$ exists abundantly. In this case, if the catalytic ability of the gas component detector is superior, the gas component as shown in the FIG. 4 will act with the remaining oxygen satisfactorily to arrive at an equilibrium and the characteristics will be changed suddenly at a point of the stoichiometric A/F ratio. However, since the catalytic ability of the gas component detector is so small, the equilibrium is not achieved and causes a shift of the position at which the characteristics change suddenly. On the other hand, in the suction control system, since the control is effected in a region where $H_2$ scarcely exists, the gases easily reach the equilibrium and the characteristics change suddenly at the point of the stoichiometric A/F ratio even if the catalytic ability is small.

SUMMARY OF THE INVENTION

In view of the foregoing, it is an object of the present invention to provide a gas component detector which can overcome the disadvantages mentioned above. According to this invention, a gas component detector is provided with a catalyst carrier body which carries thereon a catalyst material for oxidating the gas components in the detected gases and which is made of a heat-resistant metal oxide which allows the detected gases to pass therethrough. Furthermore, the catalyst carrier body is fixed by an inorganic adhesive to a holding body of an electrically insulating and heat-resistant metal oxide which supports a pair of electrodes inserted through the holding body and connected to a detector element. The catalyst carrier body encloses therein the detector element.

BRIEF DESCRIPTION OF THE DRAWINGS

FIGS. 1 to 4 are graphs of various characteristics useful to explain the prior art gas component detectors in which:

FIG. 1 is a graph of the purification percentage of harmful components v. A/F ratio;

FIG. 2 is a graph of the electrical resistance value v. A/F ratio characteristics of a gas component detector;

FIG. 4 is a graph of the gas components ($CO_2$, $H_2$ and HC) v. A/F ratio.

FIGS. 6 to 9 are graphs useful to explain the effects of the gas component detector of this invention in which;

FIG. 6 is a graph of the electrical resistance v. A/F ratio characteristics;

FIG. 7 is a graph of the control A/F ratios in the prior art and in this invention;

FIG. 8 is a graph of the control frequency in the prior art and in this invention; and FIG. 9 is a graph of the results of the endurance test.

DETAILED DESCRIPTION OF THE PREFERRED EMBODIMENTS

Figure 1:
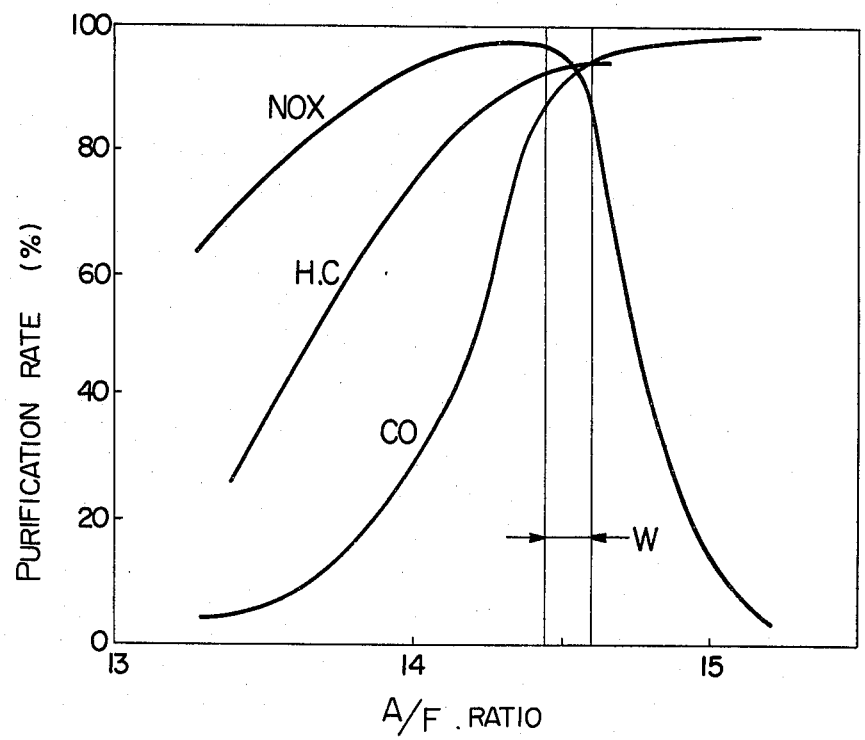
Figure 2:
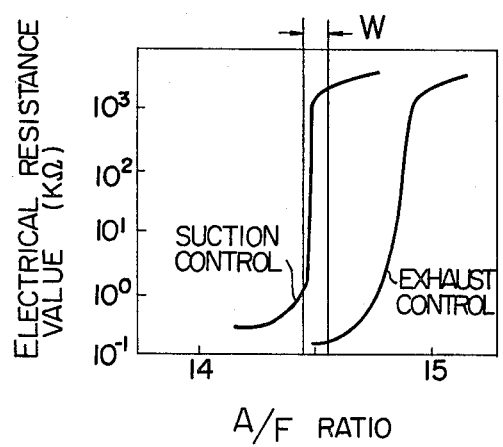
Figure 3A:
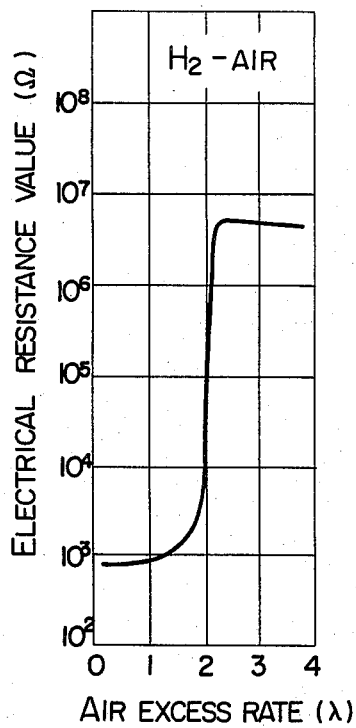
FIGS. 3a to 3c are graphs of the detection characteristics of the gas component detector in $H_2$-air, Co-air and i-$C_4H_{10}$-air environments respectively.
Figure 3B:
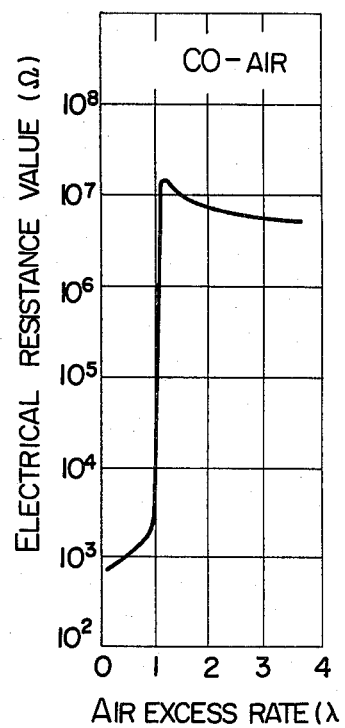
Figure 3C:
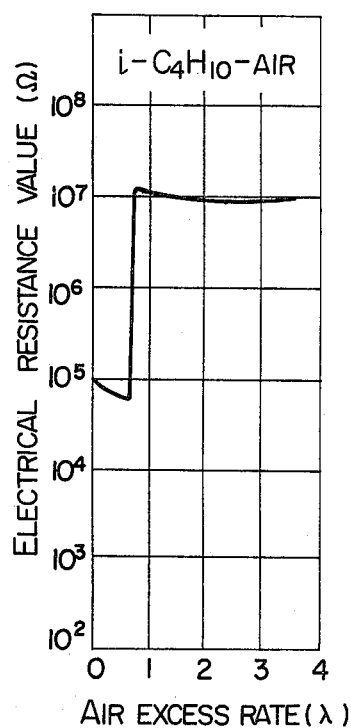
Figure 4:
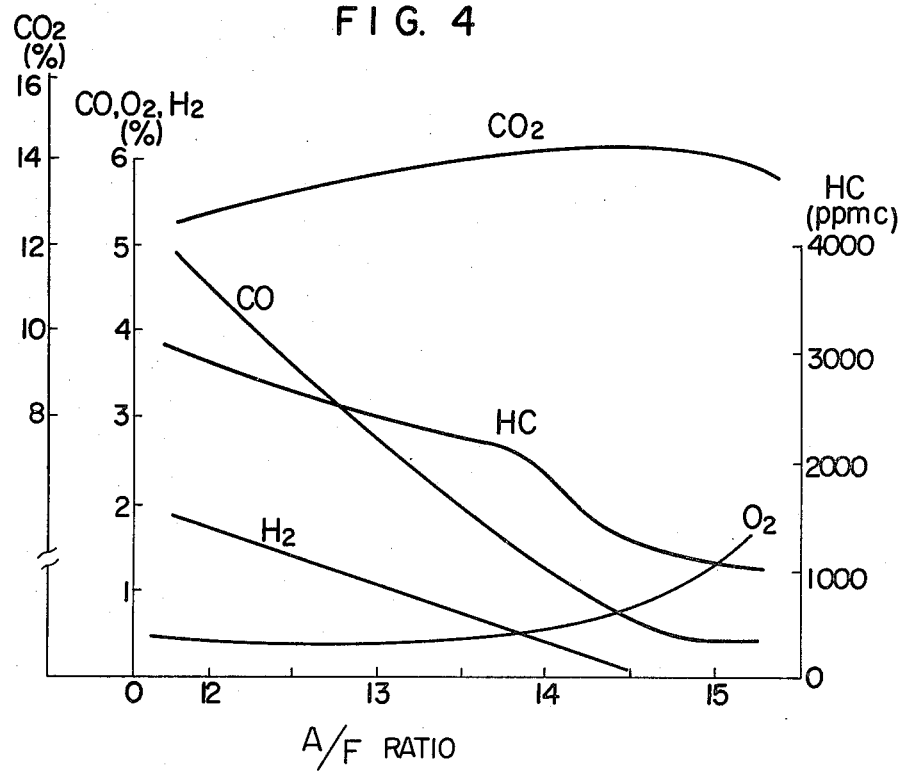
Figure 5:
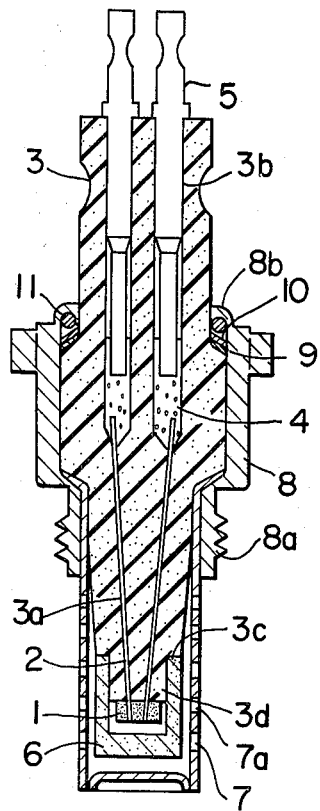
FIG. 5 is a cross-sectional view of a gas component detector according to a first embodiment of this invention.

A first embodiment will now be described referring to the drawings. In FIG. 5, 1 is a detector element comprising a sintered body of a transition metal oxide such as a titanium oxide, etc., or of a metal oxide such as a tin oxide, etc. 2 is a pair of electrodes of a heat-resistant conductive metal such as platinum, etc., buried in the detector element 1, and are inserted into a pair of small through holes 3a of a holding body 3 made of an electrically insulating and heat-resistant metal oxide such as alumina (aluminum oxide). 4 is an electrically conductive glass. 5 designates a pair of lead pins of a heat-resistant and conductive metal and are inserted into through holes 3b of the holding body 3. The lead pins 5 and electrodes 2 are conductively connected with the conductive glass 4. 6 is a bottom walled and cylindrical side walled, i.e. cup-shaped catalyst carrier of a heat-resistant metal oxide such as cordierite, alumina, etc., and it is coated with a porous heat-resistant metal oxide such as γ-alumina, etc. A catalytic material such as platinum, etc. the carrier 6 thus is provided with a well opening out of the opposite end thereof from its bottom wall is carried on the catalyst carrier 6. This catalyst carrier 6 is fixed by an inorganic bonding adhesive to a stepped portion 3c and to a straight pipe portion 3d of the holding body 3. This catalyst carrier 6 is porous so that the exhaust gases can pass therethrough. 7 is a cover of a heat-resistant metal having a number of holes 7a through which the exhaust gases can pass. 8 is a housing of a heat-resistant metal having a thread portion 8a to mount the housing 8 on the exhaust pipe of the automobile. By using ring washers 9 and 10 of a heat-resistant metal and a ring 11 of a heat-resistant metal and by caulking the upper portion 8b of the housing 8, the housing 8 is fixed to the holding body 3 airtightly.

Figure 10:
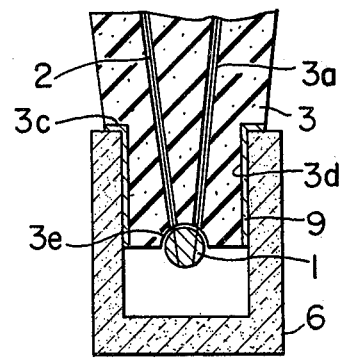
FIG. 10 is a partial cross-sectional view of a gas component detector according to a second embodiment of this invention.

FIG. 10 shows a second embodiment for this invention in which the detector element 1 is formed in a disc shape and a half-spherical concave porion 3e is provided at an end of the holding body 3. The disc-shaped detector element 1 is held in the half-spherical concave 3e so that the axis of the disc is perpendicular to the axis of the holding body 3. The other constructions are the same as the above-mentioned first embodiment.

By using the gas component detector according to the first and second embodiments, tests were conducted under the following conditions and measured the change characteristics of th electrical resistance value, the control A/F ratio and the control frequency. Furthermore, each characteristic of the prior art gas component detector which does not have the catalyst carrier 6 of the first embodiment was measured. In this description the term "control A/F ratio" means an A/F ratio detected by the gas content detector at which detected A/F ratio a feedback control of the A/F ratio is effected at the intake side or exhaust side. Further, the term "control frequency" means a frequency of generating the A/F ratio by the gas component detector.

Test Conditions:
Engine . . . 2000 cc Six cylinder, Four cycle.

Figure 6:
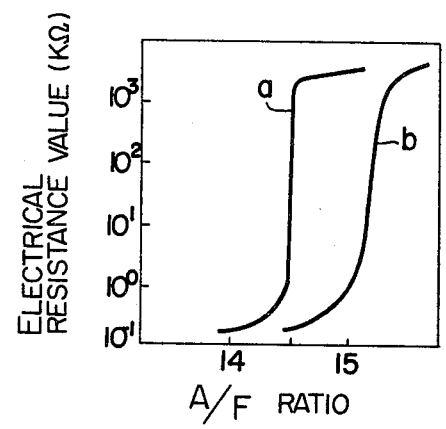
Figure 7:
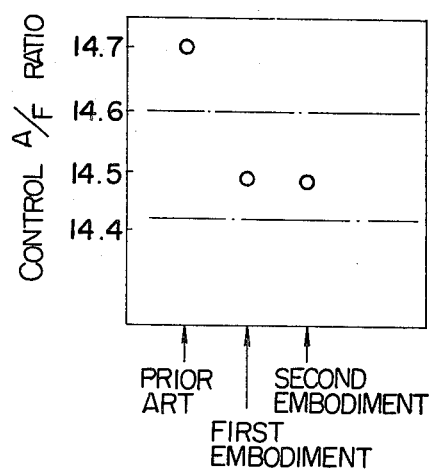
Figure 8:
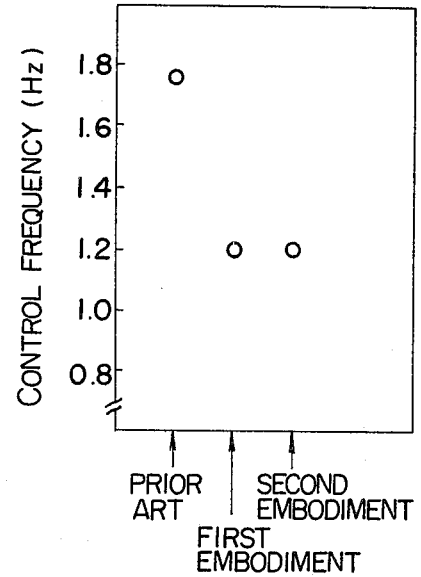

R.P.M. . . . 1600 r.p.m.
Intake vacuum pressure . . . −350 mmHg.
Temperature of the exhaust gases at the detector element portion . . . approximately 500° C.
Suction side base A/F . . . 14.0
Air pump . . . 220 cc/one rotation The above results are shown in FIG. 6 to FIG. 8. FIG. 6 shows the characteristic of a change in electrical resistance value, FIG. 7 shows the control A/F ratio, and FIG. 8 shows the control frequency. From FIG. 6 it will be seen that the electrical resistance varying point of the prior art detector (a) shifts to the lean side to a great extent whereas in the detectors (b) according to the first and second embodiments of this invention the electrical resistance value changes suddenly substantially at the point of the stoichiometric A/F ratio. From FIG. 7, it was confirmed that the control A/F ratio in the detectors of the first and second embodiments falls within the effective range of the three-way catalyst (between two chain lines in FIG. 7). Furthermore, from FIG. 8, although the control frequency is a little inferior to the prior art detector, such a degree of inferiority will cause no problem in practical use.

Next, the endurance tests in the high temperature and reducing atmosphere were conducted under the following conditions using the gas component detectors of the forementioned embodiments and the above-mentioned prior art detector.

| Test Conditions: | Evaluation Conditions: |
| --- | --- |
| Engine . . . 2000 cc | Engine . . . 2000 cc |
| Six cylinder; four cycle | Six cylinder; four cycle |
| R.P.M. . . . 4000 r.p.m. | R.P.M. . . . 1600 r.p.m. |
| Intake vacuum pressure . . . −80 mmHg | Intake vacuum pressure . . . −350 mmHg |
| Exhaust gas temperature at the detector element portion . . . approx. 800° C. | Exhaust gas temperature at the detector element portion . . . approx. 500° C. |
| Air excess rate . . . 0.8 | Air excess rate . . . 0.9 ⇌ 1.1 |

Figure 9:
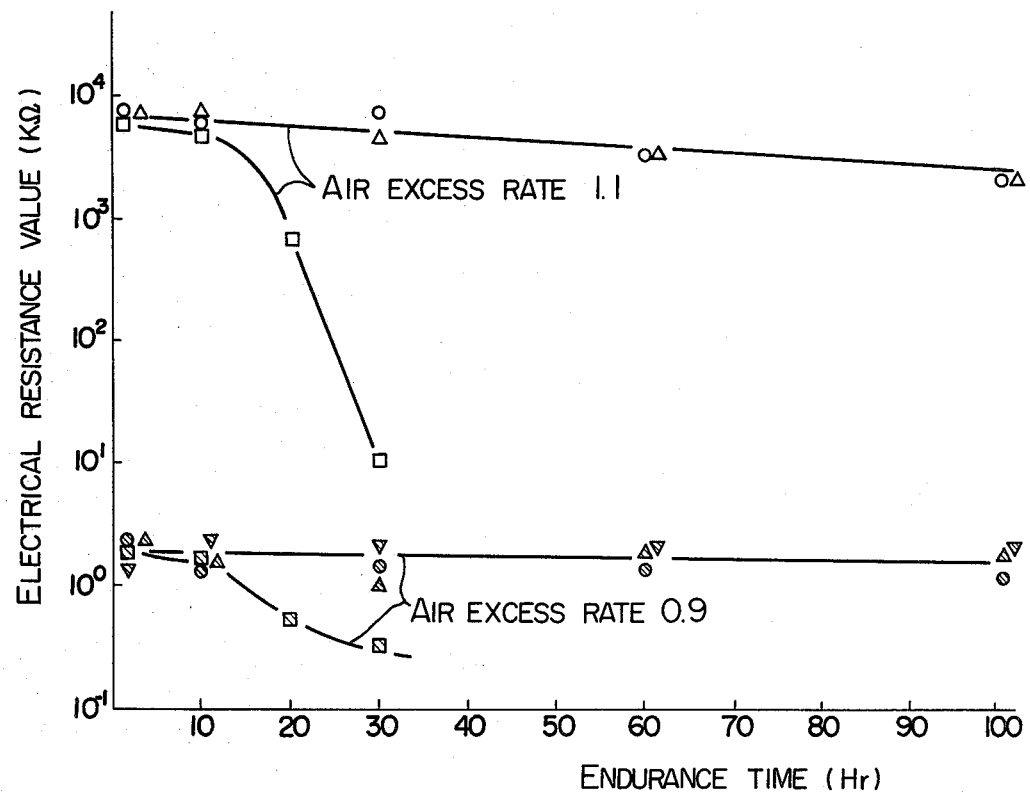

The engine was operated for a considerably long period of time under the test conditions, and during this period the measurements were conducted by switching the engine operating conditions from the test conditions to the evaluation conditions. The results are shown in FIG. 9. Mark o in FIG. 9 shows the detector of the forementioned first embodiment. Mark Δ is the detector of the forementioned second embodiment. Mark □ shows the prior art detector. In the gas component detectors of the present invention, the electrical resistance value in each of the air excess rate conditions changes very little even after the lapse of 100 hours. In contrast, the prior art detector shows a sudden change in electrical resistance value after 10 hours.

Furthermore, in the forementioned first and second embodiments, after bonding of the catalyst carrier 6 to the holding body 3 by an inorganic bonding adhesive, drying and calcining (500°–900° C.) are performed in order to raise the adhesive strength of the bonding adhesive. Thus, this process of drying and calining can advantageously be utilized as a half-melting process for the conductive glass 4 which connects conductively the lead pins 5 to the electrodes 2.

Figure 11:
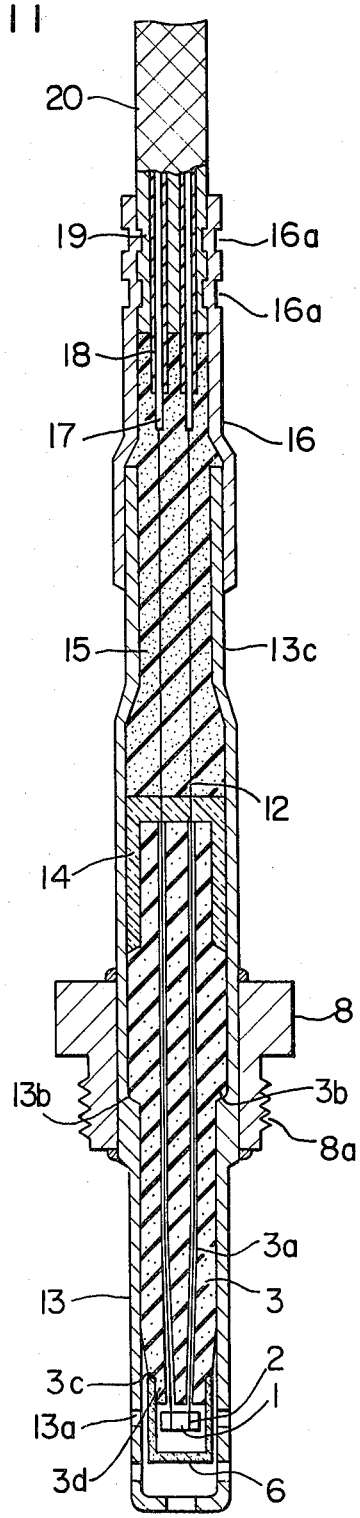
FIG. 11 is a cross-sectional view of a gas component detector according to a third embodiment of this invention.

FIG. 11 shows a third embodiment for this present invention, and a detailed description will be given as to the third embodiment. In FIG. 11, 1 is a detector element comprised of a metal oxide sintered body such as titanium oxide and tin oxide or the like. 2 is a pair of electrodes of platinum or the like buried in the detector element 1. 12 is a pair of sub-lead lines of a heat resistant metal such as stainless steel and the sub-lead lines 12 are welded to the electrodes 2 to form an electrically conducting connection therebetween. A pair of small through holes 3a having a small equal diameter in which the forementioned electrodes 2 and the sub-lead lines 12 are inserted are provided in a cylindrical holding body 3. The outer diameter of this holding body 3 is made larger at the middle portion and the body 3 is made of a heat-resistant and electrically insulating ceramic such as alumina or the like. 13 is a cover having a plurality of holes 13a for passing the exhaust gases and it also has a stepped portion 13b contacting with another stepped portion 3d of the forementioned holding body 3. The cover 13 is made of a heat-resistant metal, and the cover 13 and the ceramic body 3 are fixed together at the stepped portions 3d and 13b so as not to move. Furthermore, this cover 13 is air tightly fixed by welding to the housing 8. 14 is an inorganic glass sealing material and it becomes solid after being filled between the holding body 3 and the openings of the through holes 3a to close the openings of the through holes 3a of the holding body 3. The sealing of the exhaust gases and the insulation and fixing of the sub-lead lines 12 are ensured by this glass sealing material 15 designates an alumina powder, magnesia or the like, and ensures fixing and electrical insulation between the pair of sub-lead lines 12. 16 is a pipe of a heat-resistant metal and is fixed by welding to the forementioned cover 13. 17 is a pair of lead lines connected conductively by welding to the forementioned sub-lead lines 12. Each of covers 18 of a heat-resistant and electrically insulating material such as glass wool or heat-resistant rubber or the like covers the outside of each of the lead lines 17. Furthermore, another cover 19 of the same material as that of the cover 18 covers around the covers 18, so that the pair of lead lines 17 are electrically insulated. 20 is a cover made by knitting a heat-resistant metal and it covers the outside of the forementioned cover 19. This cover 20 is fixed to the pipe 16 by caulking the end of the pipe 16 as shown at 16a. Also, the end of the other cover 13 is chaulked as shown at 13c so that the filling density of the electrical insulating powder 15 within the cover 13 is raised.

This invention is not limited to the embodiments described above and various modifications may be possible as follows:

(1) The shape of the detector element 1 may be, of course, spherical, and the material thereof may be zinc oxide, nickel oxide and cobalt oxide, etc., besides the titanium oxide and tin oxide.

(2) The catalyst carrier 6 may be made of a foamed heat-resistant metal oxide, and the shape is not necessarily that of a circle-shaped cross section, a triangle-shaped cross-section or a horse-shoe-shaped cross section may be employed so far as the shape of the catalyst carrier enables the exhaust gases to pass therethrough and encloses the detector element 1.

(3) The catalyst material carried by the catalyst carrier is not limited to platinum, and any material such as rhodium, palladium, an alloy of these metals or other metal oxides may be used so far as these materials operate to effect oxidating reaction of the gas contents in the exhaust gases.

(4) The outside shape of the catalyst carrier may, of course be that of a construction of a bee-hive (monolith construction).

(5) It goes without saying that the gas component detector according to this invention may be used for other purposes besides the exhaust purifying operation.

According to this invention as described in detail in the foregoing, at the end of the holding body 3 of an electrically insulating and heat-resistant metal oxide, the catalyst carrier 6 made of a heat-resistant metal oxide and permitting the exhaust gases to pass therethrough is fixed to the holding body 3 by an inorganic bonding adhesive such that the catalyst carrier encloses the detector element 1. And the catalyst carrier carriers thereon a catalyst material for the oxidating reaction of the gas components in the detected gases. As a result, even if the atmosphere of the detected gases is at a high temperature and is a heavily reducing atmosphere containing carbon, the gas components of the detected gases are subjected to the oxidating reaction satisfactorily by the catalyst material of the catalyst carrier 6. Furthermore, the carbon is seized by the catalyst carrier and hence the atmosphere of the detected gases which reaches the detector element 1 becomes a weak reducing atmosphere. Therefore, the detector element 1 is seldom reduced and deteriorated due to the long-term use thereof as was the case in the prior art detector, and thus a gas component detector having a superior durability can be obtained according to this invention.

Furthermore, since the gas components in the detected gases are subjected to the oxidating reaction by the catalyst material carried on the catalyst carrier 6 as described above, even where a large quantity of unburned gas components exist in the detected gases, the unburned gas components are oxidated sufficiently and an equilibrium is reached. Thus, since the point on the electrical resistance characteristic curve at which point the resistance value changes suddenly always occurs at the same point, the gas component detector of this invention can suitably be employed in the exhaust control system which is one of the conventional exhaust gas counter-measures.

Furthermore, since in this invention, the catalyst carrier 6 is of the same material as the holding body 3 in the employment of a heat-resistant metal oxide, the catalyst carrier 6 is rarely separated from the holding body 3 due to a difference in heat expansion during usage. The firing condition between both members is maintained stable for a long period.

We claim:

1. A gas component detector comprising:
   a detector element of a metal oxide, said metal oxide exhibiting an electrical resistance value change depending upon a gas component in detected gases,
   a pair of electrodes connected to said detector element for picking up an electrical signal indicative of said electrical resistance value change,
   a holding body of an electrically insulating and heat-resistant metal oxide having a pair of through holes for supporting said pair of electrodes inserted therein,
   a cup-shaped catalyst carrier body of a heat-resistant metal oxide having a well, said catalyst carrier body being fixed to one end of said holding body to enclose said detector element within said well, said catalyst carrier body being so porous as to allow the exhaust gases to be detected to pass therethrough,
   a catalyst material carried by said catalyst carrier body for effecting oxidating reaction of said gas component in the detected gases, said cup-shaped catalyst carrier body having an internal surface of the well being spaced from the metal oxide of said detector element by an air gap with the catalyst thereon, which catalyst is not contacting the metal oxide, a cover of heat resistant metal enclosing said cup shaped catalyst carrier body, said cover having opening means provided therethrough for exposing the cup shaped catalyst carrier body to the exhaust gas.

2. A gas component detector according to claim 1, wherein said catalyst carrier body is fixed to said holding body by an inorganic bonding adhesive.

3. A gas component detector according to claim 1 wherein said holding body is provided with a half-spherical concave portion at one end thereof, and said detector element is formed in a disc shape so that said detector element is held in said half-spherical concave portion.

4. The gas component detector of claim 1, further comprising:

at the one end of said holding body a stepped reduced neck portion to affix said cup-shaped carrier body and said heat-resistant metal cover.

* * * * *